United States Patent
Chow et al.

(10) Patent No.: US 7,738,947 B2
(45) Date of Patent: Jun. 15, 2010

(54) BIOMEDICAL SIGNAL INSTRUMENTATION AMPLIFIER

(75) Inventors: Hwang-Cherng Chow, Tao-Yuan (TW); Jia-Yu Wang, Tao-Yuan (TW); Wu-Shiung Feng, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 1007 days.

(21) Appl. No.: 11/429,691

(22) Filed: May 8, 2006

(65) Prior Publication Data

US 2007/0260150 A1    Nov. 8, 2007

(51) Int. Cl.
*A61B 5/04* (2006.01)

(52) U.S. Cl. ...................................................... 600/509

(58) Field of Classification Search ................. 600/509, 600/544; 327/539; 375/320, 543; 706/66
See application file for complete search history.

(56) References Cited

U.S. PATENT DOCUMENTS

| 6,122,212 A * | 9/2000 | Bui et al. ..................... 365/207 |
| 6,569,160 B1 * | 5/2003 | Goldin et al. .................. 606/41 |

* cited by examiner

*Primary Examiner*—Carl H Layno
*Assistant Examiner*—Brian T Gedeon (57) ABSTRACT

A biomedical signal instrumentation amplifier is especially suitable for a circuit processing biomedical signals. In a voltage instrumentation amplifier, a biomedical signal level conversion circuit is added to change an input level, reduce signal distortion and noise, and achieve the performance of low voltage, unisource, low noise, high CMRR, and high PSRR.

1 Claim, 15 Drawing Sheets

|  | Conventional instrumentation amplifier | Improved instrumentation amplifier |
|---|---|---|
| Power consumption | 3.1854mW | 3.196mW |
| Differential mode gain | 39.962dB | 39.96dB |
| Common mode gain | -92.67dB | -127.22dB |
| CMRR | 132.63dB | 167.18dB |
| PSRR+ | 111.783dB | 123.407dB |
| PSRR- | 132.633dB | 112.153dB |
| Total output noise voltage (at 1 KHz) | 4.30u V/ rt hz | 5.534u V/ rt hz |
| Equivalent input noise voltage (at 1KHz) | 43.3055 n V/ rt hz | 55.596n V/ rt hz |

Table 1

BIOMEDICAL SIGNAL INSTRUMENTATION AMPLIFIER

BACKGROUND OF THE INVENTION

1. Field of the Invention

The present invention relates to a biomedical signal instrumentation amplifier and particularly to a voltage instrumentation amplifier provided with a biomedical signal level conversion circuit.

2. Description of Related Art

As technology changes with each passing day, a medical instrument is developed without exception. Because the technology of a very large scale integration (VLSI) and the concept of a System-on-a-Chip (SOC) are increasingly known, the valuable, large-scaled medical instrument is gradually being reduced and made more flexible so that it may be not only portable but also cheap and practical, thereby being widely used.

However, since late 1950's, the design and research of a biomedical signal detection system has been gradually regarded, and a biomedical signal instrument amplifier is even essential in the detection system. The biomedical signal is quite weak and different from a general electric signal, so the required biomedical signal instrumentation amplifier is different from a general amplifier.

The bandwidth of biomedical signal is part of low frequency; for example, the frequency of an electrocardiogram (ECG) signal ranges from 0.05 Hz to 100 Hz, that of an electroencephalogram (EEG) signal ranges from 0.5 Hz to 100 Hz, and that of an electro-oculogram (EOG) signal ranges from dc to 100 Hz.

The amplitude of biomedical signal is also quite weak, and where human beings stay is full of various noises that exist in the required bandwidth of biomedical signal. The noises must be filtered by a filter to reduce the impact on the biomedical signal.

When the biomedical signal from a human body is measured, a quite large common-mode voltage follows and thus in order to measure the biomedical signal that is not distorted, a biomedical signal instrumentation amplifier of an extremely high common mode rejection ratio (CMRR) is usually required to obtain the quite weak biomedical signal from a very high AC source noise.

The biomedical signal is very easily subject to the interference of an external signal and that of a physiology signal from a person under test, so it is more difficult to measure the signal, in which internal interference comprises noises of MOS and problems of wire layout in a circuit, and external interference comprises electromagnetic waves caused by AC source and noises caused by instable power. The physiology signal as interference comprises the EOG signal, myoelectric signal, the ECG signal and the like, and thus it is important to design the instrumentation amplifier of high CMRR to restrain the common mode noises and precisely amplify the minute biomedical signal.

Generally, the instrumentation amplifier may be on the whole divided into:

(1) a voltage-based instrumentation amplifier, and
(2) a current-based instrumentation amplifier.

Figure 1:
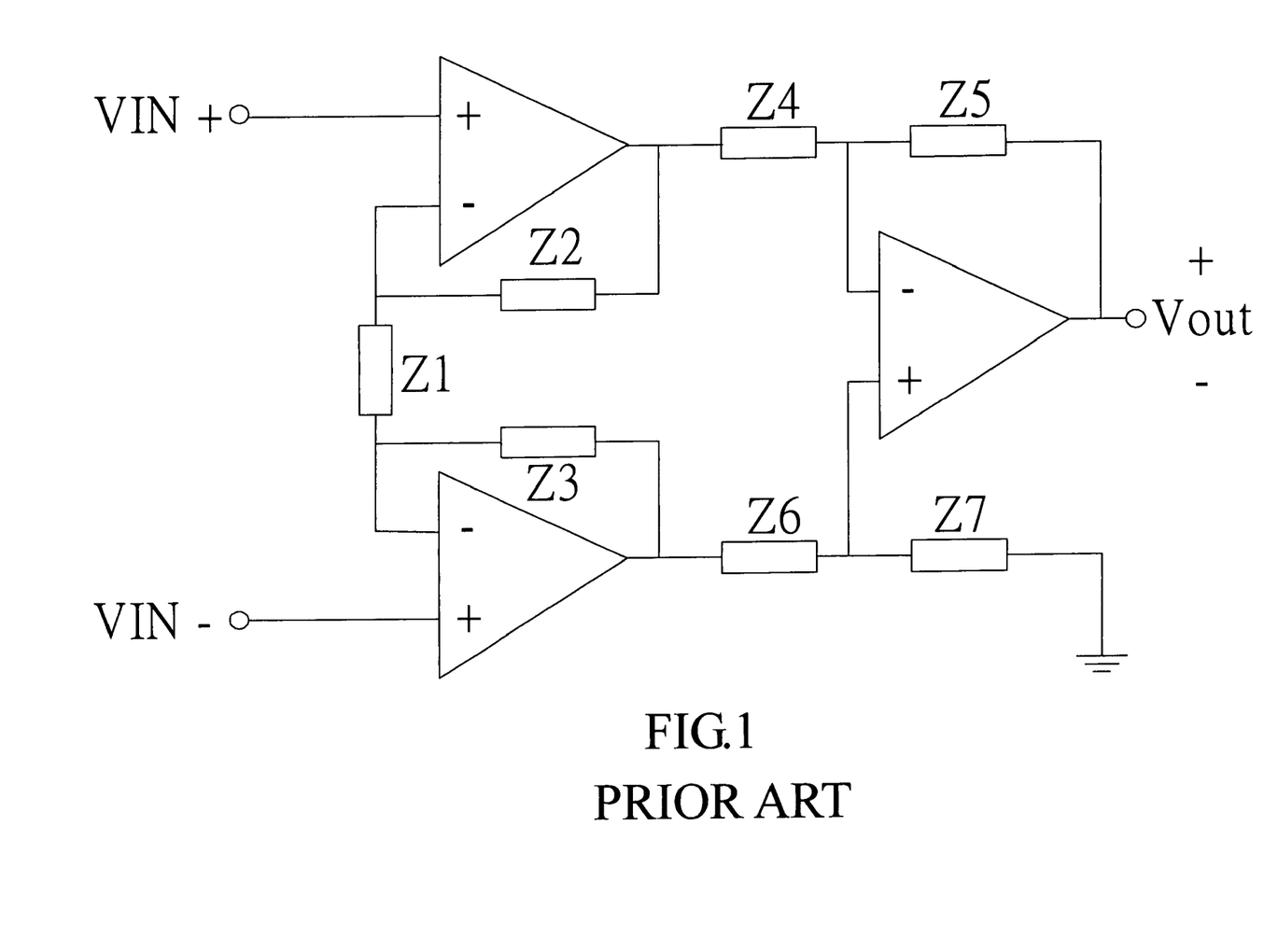
FIG. 1 is a view of a conventional voltage-based instrumentation amplifier.

Most technical literatures describe the design of voltage-based instrumentation amplifier. As shown in FIG. 1, the hardware is structured with 3 voltage-based operation amplifiers and 7 resistors as passive elements. A drawback is that the high CMRR is limited to the match capability of the resistors and the resistors must occupy a large area for precise values and their match capability at the time of wire layout.

Contrarily, a standard current-based instrumentation amplifier is formed with a current conveyor, of which the matching capability is not comparatively a problem but is accomplished requiring only a small number of resistors; the required passive elements are fewer for easy control of gain. Although the common mode rejection is higher than that of a conventional voltage-based instrumentation amplifier, the number of resistors and the size of each resistor relatively impacts on thermal noise; however, the entire circuit is huge. Thus, in order to effectively solve new problems derived from power consumption, circuit performance, and noises, a new structure must be provided to find an optimal circuit.

In the design of an instrument system, an amplifier is required to block a large interference noise signal that is a signal (common-mode signal) shared by two lead wires, and amplify a weak differential signal, in which the amplifier is generally called instrumentation amplifier.

Figure 2:
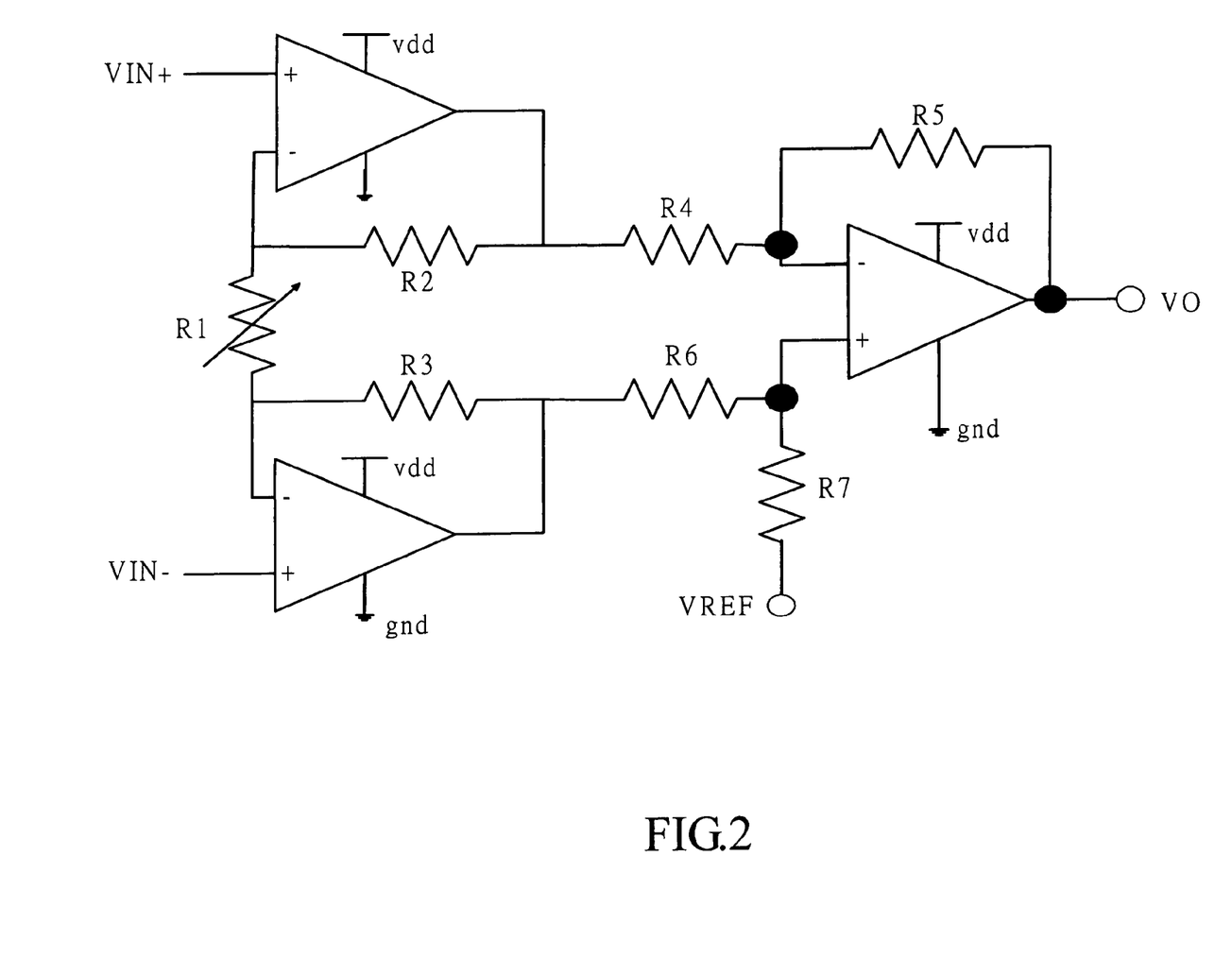
FIG. 2 is a view of a conventional voltage-based instrumentation amplifier with a unisource.

As shown in FIG. 2, a conventional instrumentation amplifier is formed with a plurality of passive elements.

For achievement of the high-performance CMRR and power supply rejection ratio (PSRR), in addition to the requirements of low output impedance and high voltage gain and the requirement of perfect impedance matching of passive elements in the circuit, the conventional voltage-based instrumentation amplifier must satisfy the area requirement for the accuracy, so this invention is to provide the new structure to reduce the passive elements and the noises and meanwhile enhance the performance of circuit.

Consequently, because of the technical defects of described above, the applicant keeps on carving unflaggingly through wholehearted experience and research to develop the present invention, which can effectively improve the defects described above.

SUMMARY OF THE INVENTION

In order to solve the above problems, a conventional voltage-based instrumentation amplifier is structured with 3 voltage-based operation amplifiers and 7 resistors as passive elements so that high CMRR is limited to the match capability of the resistors and the resistors must occupy a large area for precise values and their match capability at the time of wire layout; although the CMRR of current-based instrumentation amplifier is higher, thermal noise easily occurs with respect to the amount of resistors and the size and each resistor.

To solve the technical problems, a biomedical signal instrumentation amplifier is provided, of which an input terminal is a biomedical signal level conversion circuit. The biomedical signal level conversion circuit is connected to first and second voltage-to-current operation amplifiers, and the signals from the first and second voltage-to-current operation amplifiers are amplified by a differential amplifier.

For a virtue compared with that of the prior art, the biomedical signal instrumentation amplifier is provided to reduce the amount of resistors, the thermal noise, and the variation errors of the resistances in a manufacturing process, and with the accuracy of a current mirror, the capability of matching to circuits is enhanced, thereby the performance of CMRR and PSRR increasing.

However, in the description mentioned above, only the preferred embodiments according to the present invention are provided without limit to the present invention and the characteristics of the present invention; all those skilled in the art without exception should include the equivalent changes and modifications as falling within the true scope and spirit of the present invention.

DETAILED DESCRIPTION OF THE PREFERRED EMBODIMENTS

Now, the present invention will be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, the design of a biomedical signal instrumentation amplifier is provided.

Figure 3:
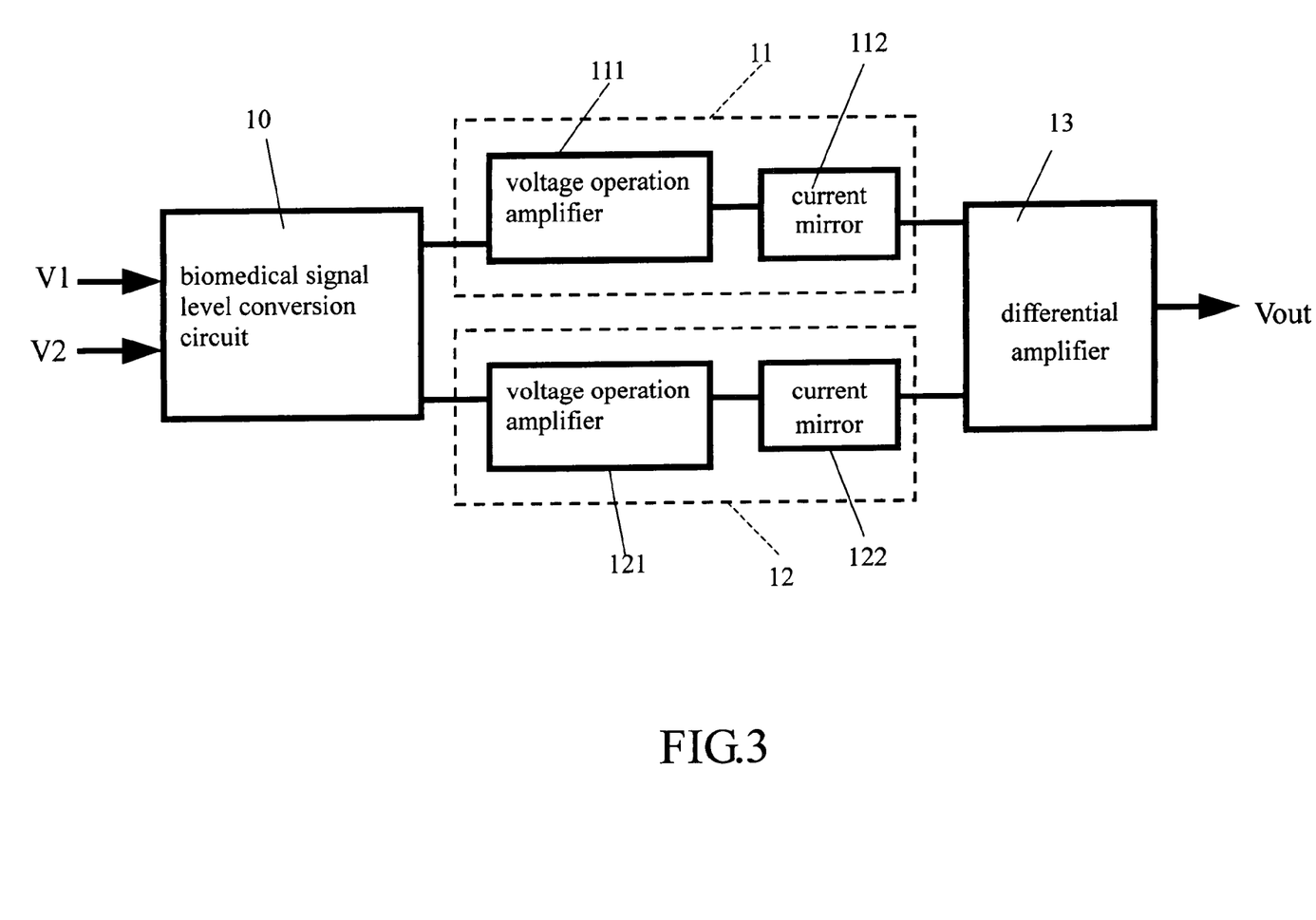
FIG. 3 is schematic view illustrating the structure of a biomedical signal instrumentation amplifier according to this invention.

At first, referring now to FIG. 3 as schematic view illustrating the structure of biomedical signal instrumentation amplifier according to the present invention, of which an input terminal is a biomedical signal level conversion circuit (10). The circuit is designed into a unisource structure, so an original weak biomedical signal level must be raised to an input level required for the biomedical instrumentation amplifier. In order to raise CMRR, a biomedical signal level conversion circuit (10) is connected to a first voltage-to-current operation amplifier (11) and a second voltage-to-current operation amplifier. (12). The first voltage-to-current operation amplifier (11) and the second voltage-to-current operation amplifier (12) are structured with voltage operation amplifiers (111) and (121) that are connected to current mirrors (112) and (122) for replacement of resistors as passive elements, and convert input voltage into current of which a signal is amplified by a differential amplifier (13). Thus, the amount of resistors and thermal noise may be reduced and the variation errors of the resistances in a manufacturing process may further be reduced. Also, with the accuracy of the current mirrors, the capability of matching to circuits is enhanced, thereby the performance of CMRR and PSRR increasing.

Figure 4:
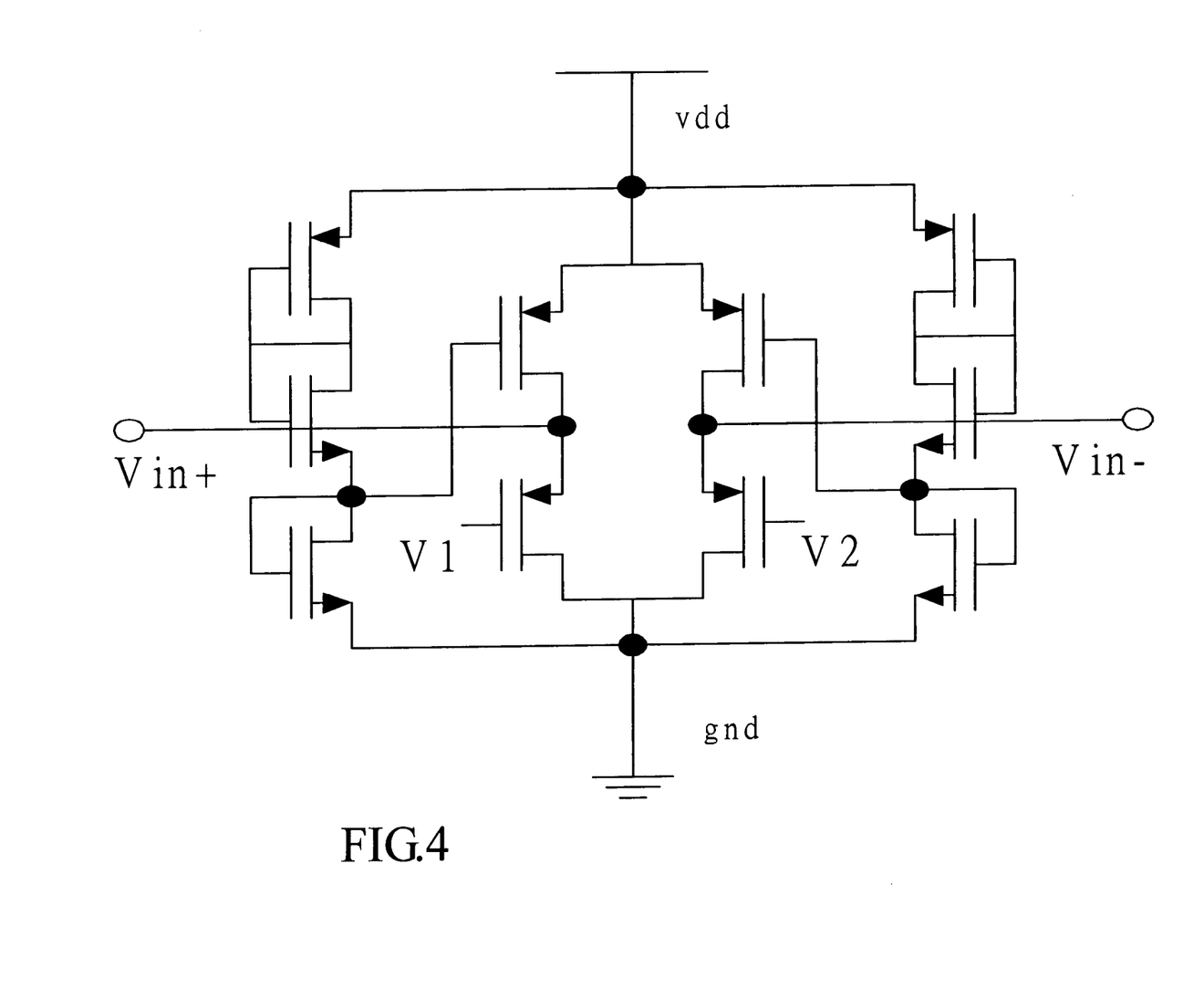
FIG. 4 is a diagram of a level conversion circuit for the biomedical signal processing according to this invention.

FIG. 4 is a diagram of a level conversion circuit for the biomedical signal processing. When an electrode pad senses a weak biomedical signal and connects to two input terminals of V1 and V2, the signal varies at a DC level of around 0V. Because PMOS accepts a negative voltage below 0V, after the conversion of voltage level, the voltage levels of V1 and V2 are raised to VIN+ and VIN−, higher DC levels, so as to drive and use an input common-mode level of an improved instrumentation amplifier. Further, I/O transistors are structured with PMOS, since PMOS may be given an independent NWELL to isolate a conduction noise from a p-substrate, thereby the distortion caused by the interference of weak signal being reduced.

Figure 5:
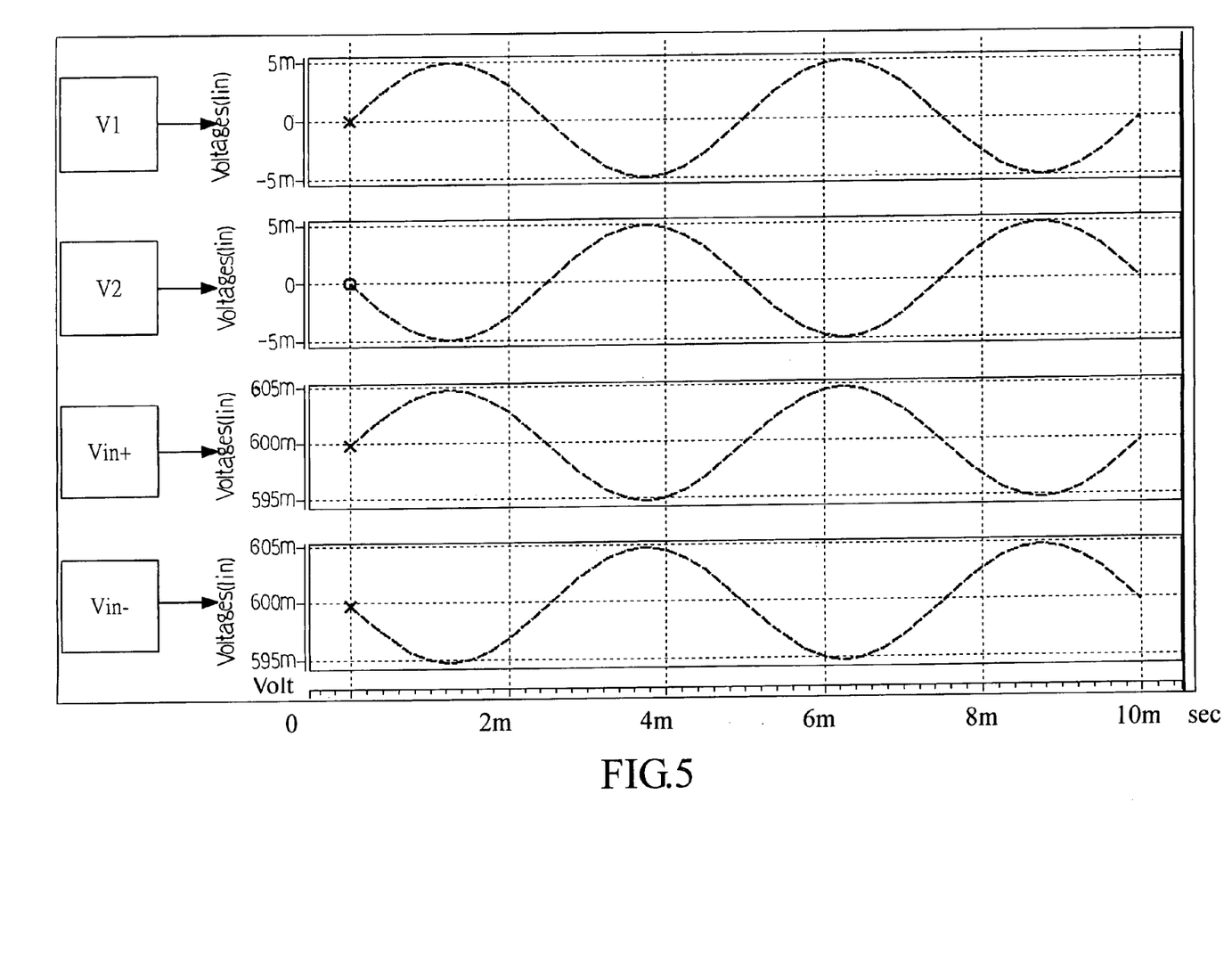
FIG. 5 is a chart explaining a result from the simulation of level conversion circuit for the biomedical signal processing according to this invention.

FIG. 5 is a chart explaining a result from the simulation of level conversion circuit for the biomedical signal processing. V1 and V2 are maximum ECG signal amplitudes of an adult (±5 mV). Vin+ and Vin− are the results outputted by the level conversion circuit required for the biomedical signal processing, and the DC level may be raised to a level of 0.6V.

Figure 6:
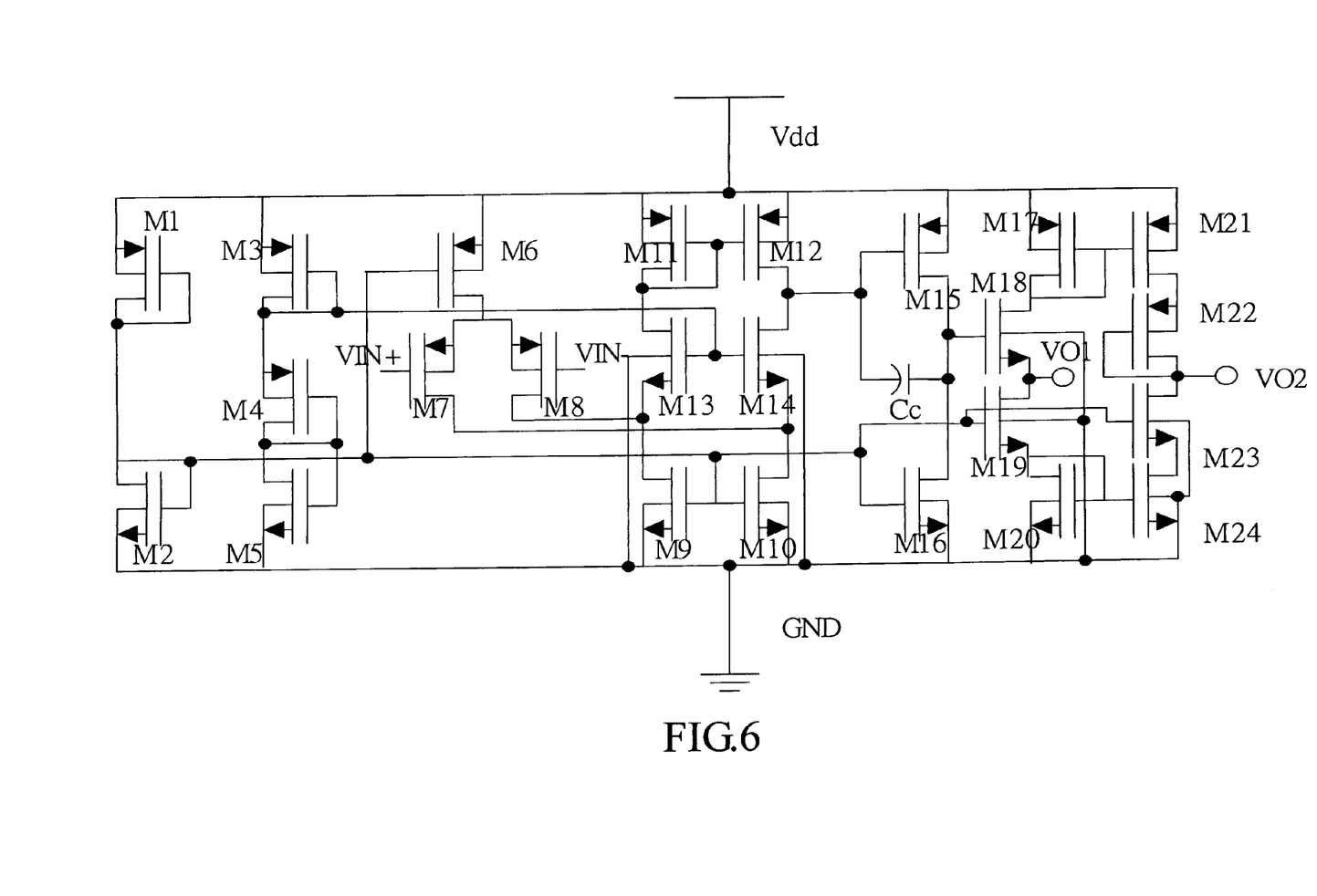
FIG. 6 is a diagram of a voltage-to-current operation amplifier according to this invention.

FIG. 6 is a diagram of a voltage-to-current operation amplifier according to this invention. The VIN+ and VIN− of operation amplifier are voltage input terminals; the Vo1 and Vo2 output terminals of operation amplifier are current output terminals cascaded with two sets of current mirrors to sense the variation of a voltage at the input terminal and output current; the output terminal of Vo2 is cascaded through MOS to make the impedance increase for reduction of noise interference caused between Vdd and GND and for increasing the PSRR; Cc is a Miller compensating capacitor.

Figure 7:
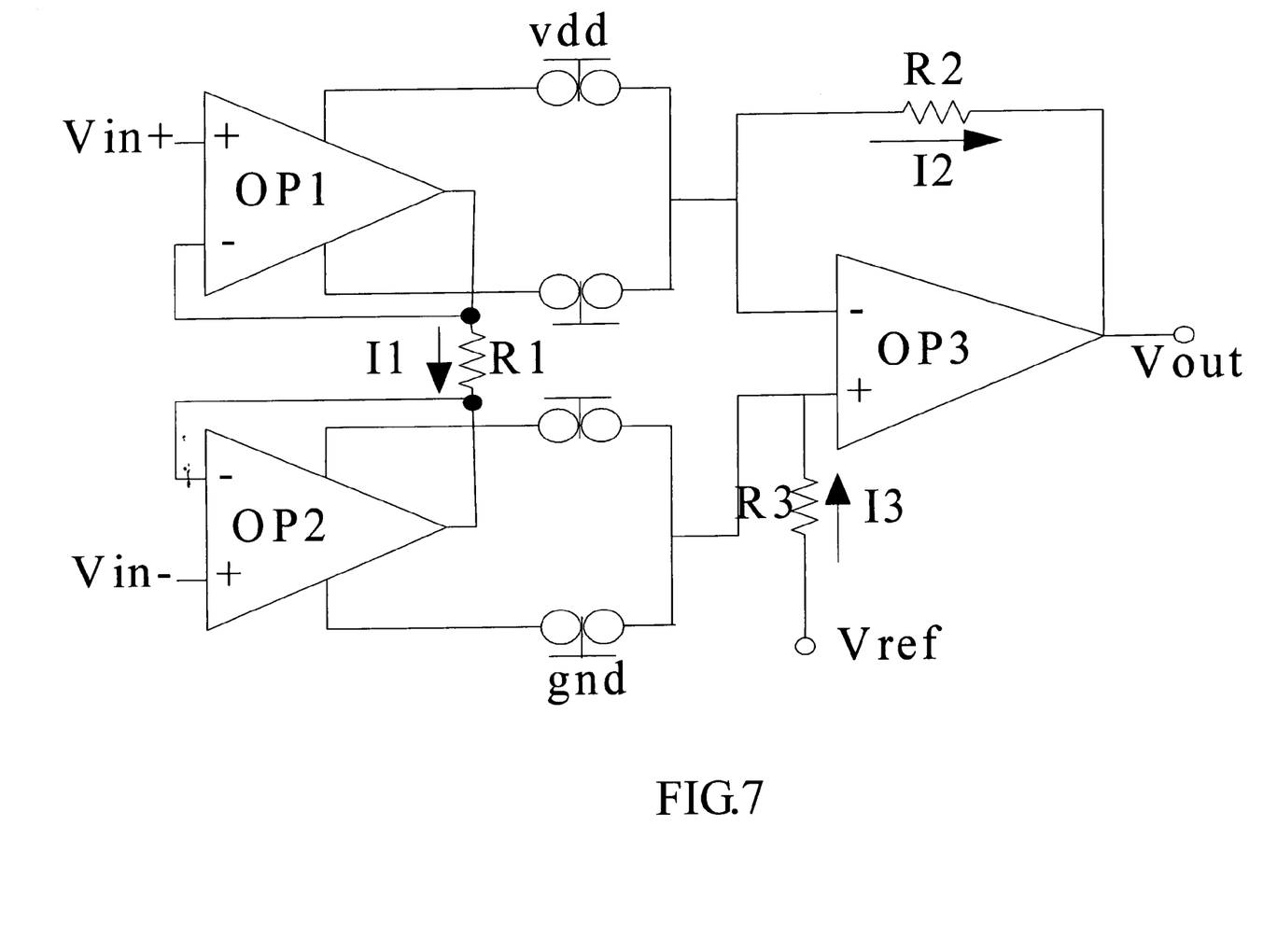
FIG. 7 is schematic view illustrating the structure of a voltage-to-current instrumentation amplifier according to this invention.

As shown in FIG. 7 illustrating the structure of a voltage-to-current instrumentation amplifier according to the present invention, three improved operation amplifiers and three resistors as passive elements are provided. The circuit is designed to work in a unisource mode.

Figure 8:
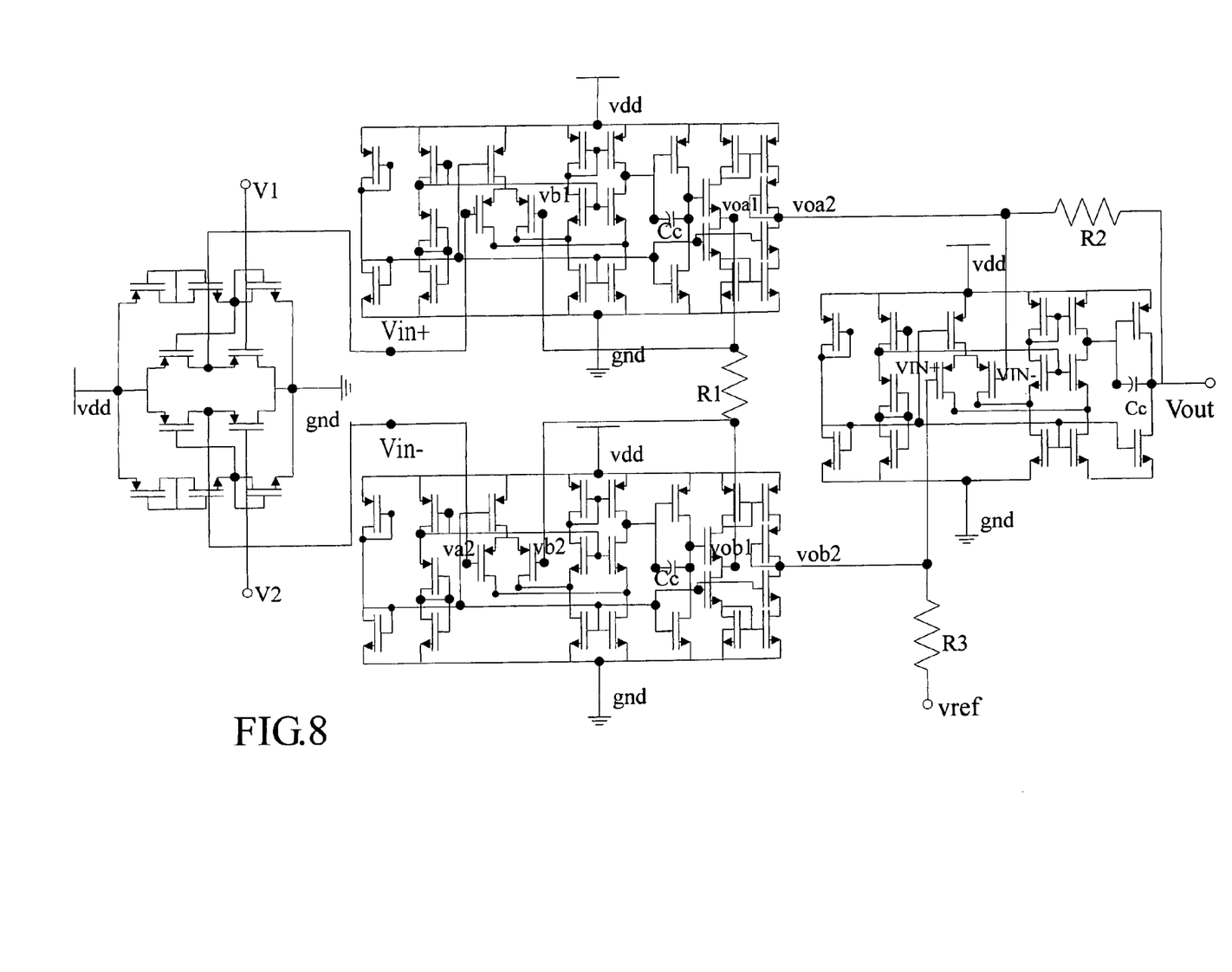
FIG. 8 is a diagram of the detailed circuit of biomedical signal instrumentation amplifier according to this invention.

FIG. 8 is a diagram of the detailed circuit of biomedical signal instrumentation amplifier according to the present invention. The biomedical signal is too weak to provide an input common-mode level from the instrumentation amplifier, so the signal must pass through the level conversion circuit so as to raise the voltage level of an original biomedical signal, thereby the input level from the instrumentation amplifier being provided. V1 and V2 are weak biomedical signals measured from the human body through the electrode pad, and after the signals are converted by the level conversion circuit, the biomedical signal levels are raised to a common mode input range in which the biomedical instrumentation amplifier may operate.

Figure 9:
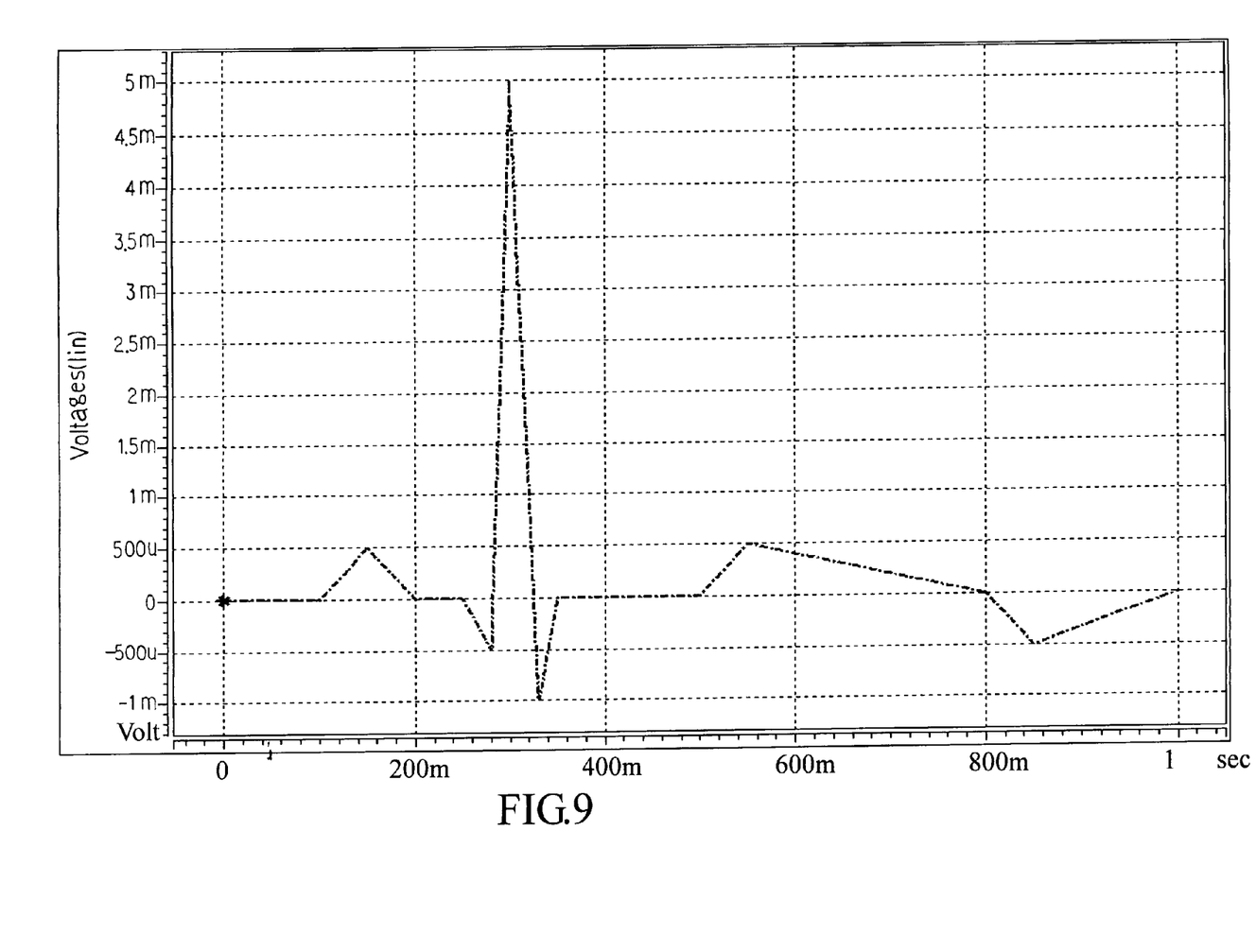
FIG. 9 is a chart of an approximately real physiological signal graph of ECG simulated with triangular waves.

FIG. 9 is a chart of an approximately real physiological signal graph of ECG simulated with triangular waves, in which the amplitude is 5 mV (maximum from an adult) and the cycle is 1 second (around 60 heartbeats in a minute). It is assumed that the ECG signal measured from the electrode pad is quite weak and varies at a common mode level of 0V.

Figure 10:
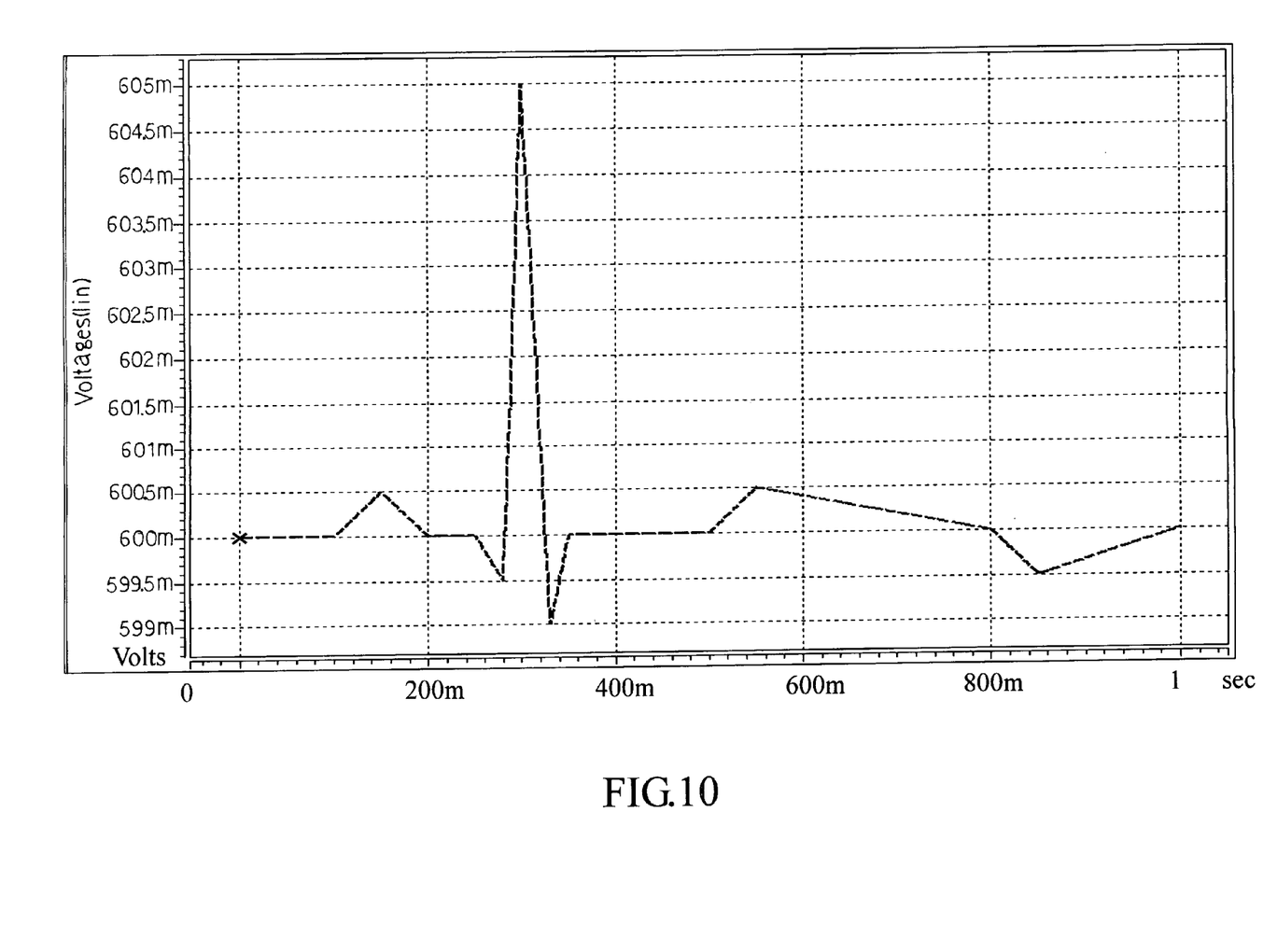
FIG. 10 is a chart of a biomedical signal simulated from the level conversion circuit for the biomedical signal processing.

FIG. 10 is a chart illustrating a result of the biomedical signal given from the level conversion circuit for the biomedical signal processing. From the simulation result, the voltage level of the ECG signal is raised from 0V to 600 mV, and the signal amplitude completely reflects the signal source without serious distortion or attenuation.

Figure 11:
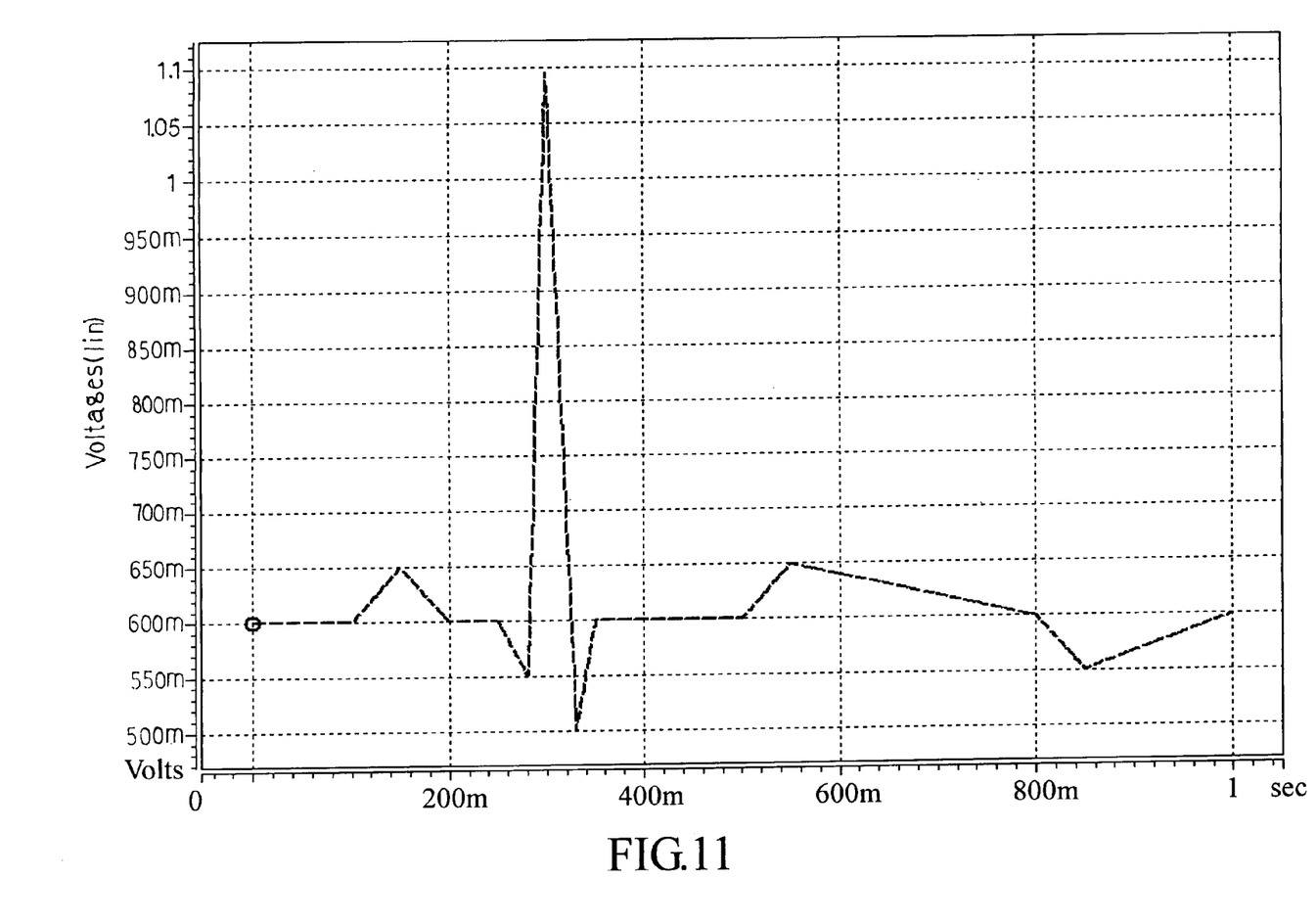
FIG. 11 is a resulting simulation chart of the ECG signal amplified by the instrumentation amplifier.

FIG. 11 is a resulting simulation chart of the ECG signal amplified by the instrumentation amplifier. After being processed by a level adjustment circuit, the original physiological signal of ECG is sent to the improved instrumentation amplifier. In the resulting simulation chart of biomedical signal amplified .times.100 times (40 dB) by an instrumentation amplification circuit, an expected result is shown.

Figure 12:
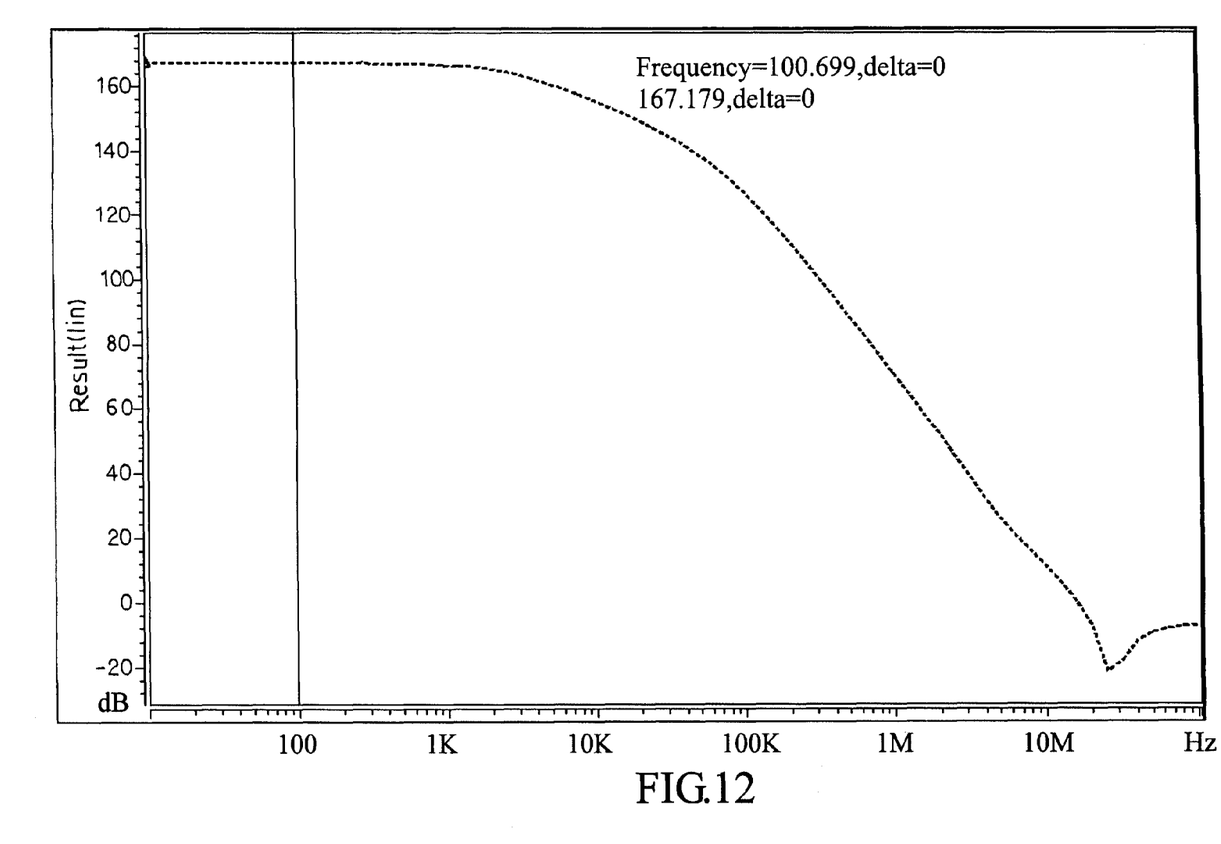
FIG. 12 is a resulting CMRR simulation graph of a complete circuit.

FIG. 12 is a resulting CMRR simulation graph of a complete circuit, in which a value is 167.179 dB.

Figure 13:
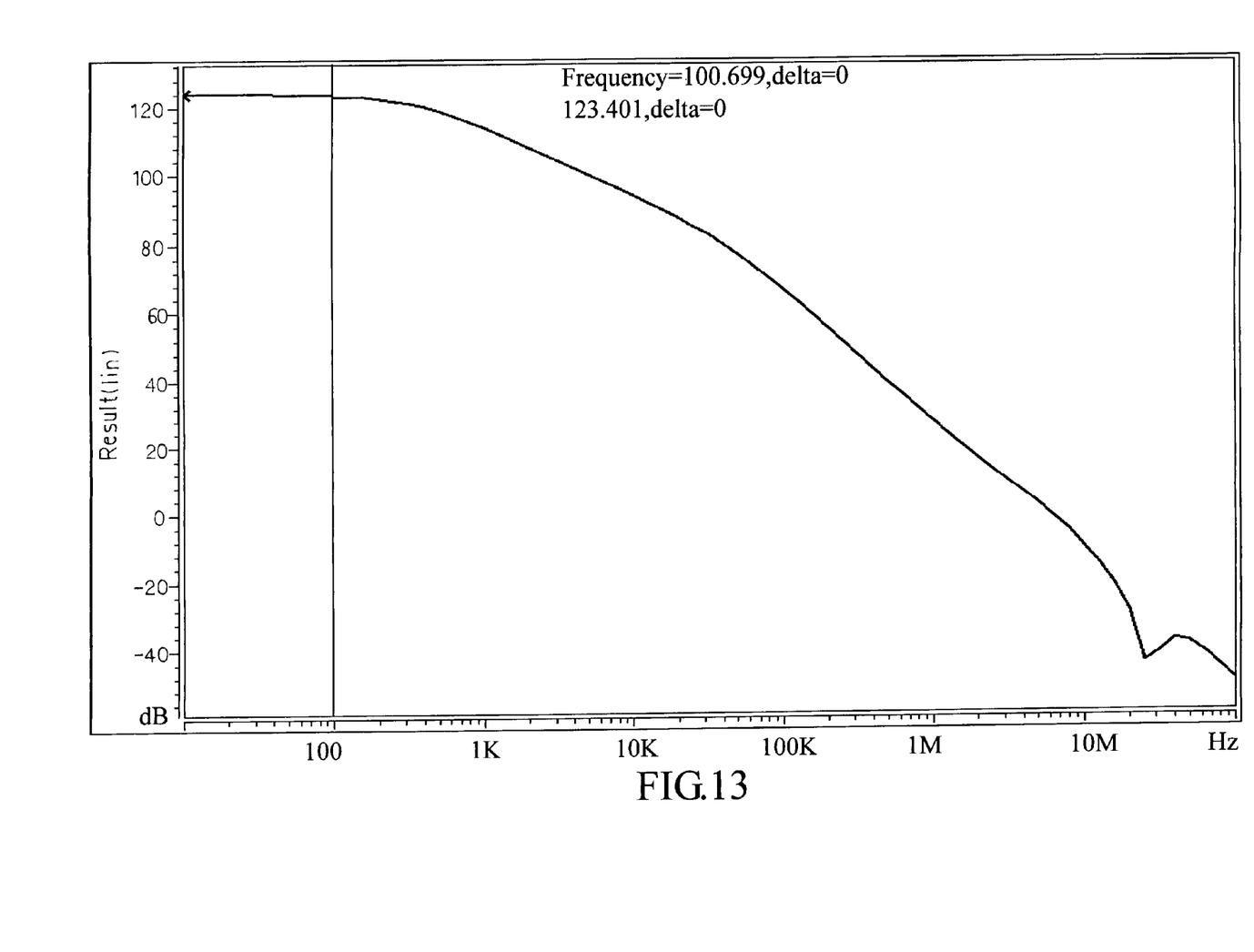
FIG. 13 is a resulting positive PSRR simulation graph of the complete circuit.

FIG. 13 is a resulting positive PSRR (PSRR+) simulation graph given from the complete circuit, in which a value is 123.4 dB.

Figure 14:
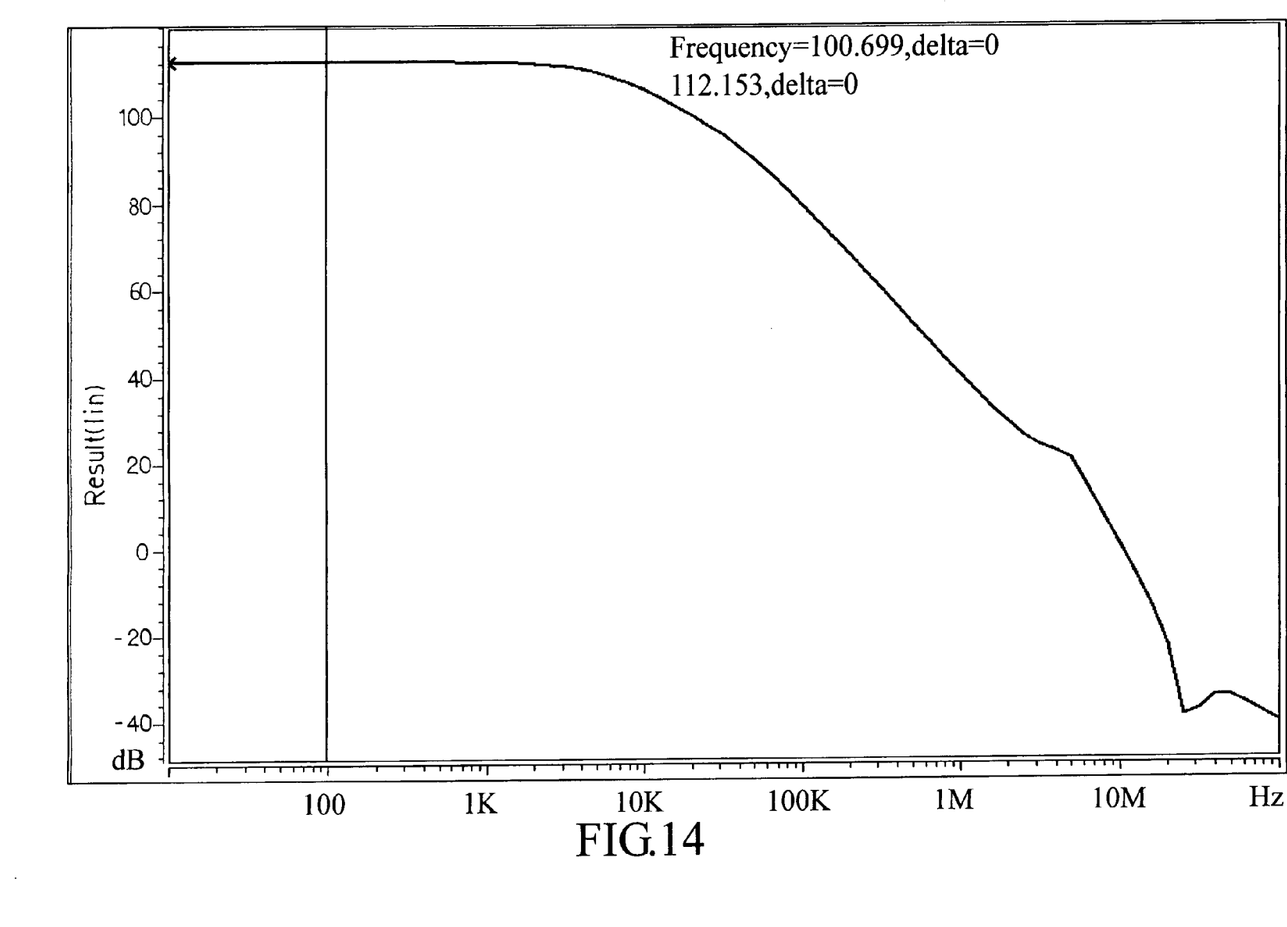
FIG. 14 is a resulting negative PSRR simulation graph of the complete circuit; and Table 1 gives a result from the comparison of a conventional voltage-based instrumentation amplifier with an improved voltage-based instrumentation amplifier.

FIG. 14 is a resulting negative PSRR (PSRR−) simulation graph given from the complete circuit, in which a value is 112.153 dB.

Table 1 gives a result from the comparison of a conventional voltage-based instrumentation amplifier with an improved voltage-based instrumentation amplifier. Under the conditions of a supply voltage of 1.8 V, a temperature of 25° C., a typical model, close power consumption, and an equal size of the structure of operation amplifier as possible as they can be, the characteristics of the two amplifiers are simulated and compared. From the result of simulation, it is apparent that the improved instrumentation amplifier is provided with better characteristics at CMRR and PSRR+. However, the whole noise outputted from the improved instrumentation amplifier is more than that from the conventional instrumentation amplifier, since the current passing through the current mirror is copied with precise current in order to lower the output resistances of Vo1 and Vo2. Thus, the elements are enlarged, but MOS is a resistor of high resistance when working at a saturation region, and thus more significant thermal noise phenomenon occurs; nevertheless, the output noise is kept in an acceptable range of the biomedical signal.

To sum up, in the present invention, the passive elements in the circuit of conventional instrumentation amplifier are improved. The circuit is changed into a current mirror circuit to make CMRR and PSRR increase. With the circuit according to the present invention, the conventional circuit is improved for:

1. CMRR that is raised up to 26%, and
2. PSRR+that is raised up to 10.39%

While the present invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A biomedical signal instrumentation amplifier, comprising: a biomedical signal level conversion circuit of unisource design for a single working voltage including a conversion circuit that raises an original differential biomedical signal voltage level to an input level required for a first voltage-to-current operation amplifier and a second voltage-to-current operation amplifier; a first voltage-to-current operation amplifier and a second voltage-to-current operation amplifier, in which the voltage-to-current operation amplifier is a voltage amplifier cascaded with a current mirror to output a voltage signal from the biomedical signal level conversion circuit; and a differential amplifier for receiving signals from the first voltage-to-current operation amplifier and the second voltage-to-current operation amplifier and amplifying and then producing an output signal from them.

* * * * *